United States Patent
Biksacky

(10) Patent No.: US 9,442,047 B2
(45) Date of Patent: Sep. 13, 2016

(54) SEGMENTED ONLINE SAMPLING APPARATUS AND METHOD OF USE

(71) Applicant: Flownamics Analytical Instruments, Inc., Madison, WI (US)

(72) Inventor: Michael J. Biksacky, Madison, WI (US)

(73) Assignee: Flownamics Analytical Instruments, Inc., Madison, WI (US)

( * ) Notice: Subject to any disclaimer, the term of this patent is extended or adjusted under 35 U.S.C. 154(b) by 278 days.

(21) Appl. No.: 14/047,719

(22) Filed: Oct. 7, 2013

(65) Prior Publication Data
US 2014/0033834 A1 Feb. 6, 2014

Related U.S. Application Data

(62) Division of application No. 12/410,246, filed on Mar. 24, 2009, now Pat. No. 8,549,934.

(60) Provisional application No. 61/039,266, filed on Mar. 25, 2008.

(51) Int. Cl.
*G01N 1/20* (2006.01)
*G01N 35/08* (2006.01)

(52) U.S. Cl.
CPC ............ *G01N 1/2035* (2013.01); *G01N 35/08* (2013.01); *G01N 2001/205* (2013.01)

(58) Field of Classification Search
None
See application file for complete search history.

(56) References Cited

U.S. PATENT DOCUMENTS

| | | | |
|---|---|---|---|
| 3,482,450 A | 12/1969 | Harris, Jr. et al. | |
| 3,668,936 A | 6/1972 | Herron | |
| 3,759,667 A * | 9/1973 | Bannister et al. | B01L 3/0293 141/130 |
| 3,974,697 A | 8/1976 | Speth | |
| 3,990,312 A | 11/1976 | Koukol | |
| 5,080,866 A | 1/1992 | Petty et al. | |
| 5,380,665 A | 1/1995 | Cusack | |
| 5,487,313 A * | 1/1996 | Johnson | G01N 30/16 73/23.42 |
| 5,547,875 A | 8/1996 | Petty et al. | |
| 5,834,314 A | 11/1998 | Gates et al. | |
| 6,130,098 A * | 10/2000 | Handique | B01F 5/0085 366/DIG. 2 |
| 6,203,759 B1 | 3/2001 | Pelc et al. | |
| 6,289,714 B1 | 9/2001 | Tartre | |
| 6,432,721 B1 | 8/2002 | Zook et al. | |
| RE38,281 E * | 10/2003 | Tisone | B01L 3/0265 118/305 |
| 6,689,621 B2 | 2/2004 | Merten et al. | |
| 6,706,535 B2 | 3/2004 | Sacks et al. | |
| 7,059,352 B2 * | 6/2006 | Bohm | F16K 99/00 137/828 |
| 7,156,117 B2 * | 1/2007 | Bohm | G05D 7/0694 137/14 |
| 2002/0141903 A1 * | 10/2002 | Parunak | B01L 3/502738 422/504 |

(Continued)

FOREIGN PATENT DOCUMENTS

| | | |
|---|---|---|
| EP | 0848242 | 6/1998 |
| WO | 03093323 | 11/2003 |

OTHER PUBLICATIONS

European Appln. No. 09156180.3—EP Communication dated May 27, 2014, 6 pages.

*Primary Examiner* — Hezron E Williams
*Assistant Examiner* — Mark A Shabman
(74) *Attorney, Agent, or Firm* — Boyle Fredrickson, S.C.

(57) ABSTRACT

A segmented sampling apparatus is designed to extract a sample from a source and deliver the sample to a collector for storage or analysis. The sample is extracted from the source at a sample withdrawal or extraction rate but is delivered to the collector at a faster rate. Air is injected into or drawn into the apparatus which allows for an expedited sample delivery rate.

4 Claims, 16 Drawing Sheets

(56) References Cited

U.S. PATENT DOCUMENTS

| | | |
|---|---|---|
| 2002/0192113 A1 | 12/2002 | Uffenheimer et al. |
| 2003/0230486 A1* | 12/2003 | Chien ................ B01F 13/0076 204/450 |
| 2004/0109386 A1* | 6/2004 | Gold ..................... B01F 5/0646 366/336 |
| 2004/0178917 A1 | 9/2004 | Duan |
| 2004/0232080 A1 | 11/2004 | Neyer et al. |
| 2005/0220629 A1* | 10/2005 | Bohm ............... B01L 3/502784 417/53 |

* cited by examiner

SEGMENTED ONLINE SAMPLING APPARATUS AND METHOD OF USE

CROSS-REFERENCE TO RELATED APPLICATION

This application is a divisional of application Ser. No. 12/410,246 filed Mar. 24, 2009, which claims the benefit of U.S. Ser. No. 61/039,266, filed Mar. 25, 2008.

BACKGROUND AND SUMMARY OF THE INVENTION

The present invention relates generally to sampling systems, and more particularly, to a sampling apparatus that can draw a sample from a source at one rate and deliver the sample to a collector system, such as an analyzer or sampler reservoir, at a different rate.

Sampling systems are commonly used to draw a sample from a sample source, commonly contained in a bioreactor vessel, and deliver the sample to an analyzer, collector, or other device, such as an autosampler. Many sampling systems utilize a pump to withdraw the sample from the sample source and pass the sample along a line of conduit or other tubing to the autosampler or other collector. Many sampling systems require a relatively slow flow rate to withdraw the sample from the sample source to prevent clogging of the tubing/membrane, degassing in the tubing, and to otherwise extend the useful life of the sampling system.

On the other hand, it is generally preferred to deliver a small sample to the collector or analyzer to reduce sample loss and to deliver it quickly to avoid chemical/biological changes in the sample or future samples from the sample source or sources if multiple sample sources are sampled therefrom. Conventional sampling systems, as noted above, use a relatively slow flow rate and, as such, larger samples must be drawn from the sample source to account for the loss of sample during the withdrawal and delivery process. Using larger samples accelerates the depletion of sampling material from the source, which can be particularly undesirable when sampling cellular and/or biological material.

The present invention is directed to a segmented online sampling apparatus that captures a fluid sample, such as a biological sample from a bioreactor, fermentation vessel, or process stream without the significant loss of cells, biological material, media, or other material. In general, the sampling apparatus allows a sample to be withdrawn from a source at one sampling flow rate yet delivered by a delivery system to a collector, analyzer, or sample reservoir at a different flow rate.

According to one aspect of the invention, a sampling system includes a sample withdrawal system that is operative to withdrawal a sample from a source at a sample withdrawal flow rate, and also includes a sample collector system operative to receive the sample. The sampling system also includes a sample delivery system that is operative to deliver the sample from the sample withdrawal system to the sample collector system at a sample delivery flow rate that is different than the sample withdrawal flow rate.

In accordance with another aspect of the invention, a sampling apparatus for extracting a sample from a source and presenting the sample to a collector includes an intake port adapted to receive a sample from the source at a first flow rate, and a first valve that is flow coupled to the intake port to control the acquisition of the sample from the source and presentation of the sample to a line. The apparatus also has a second valve that is flow coupled to a fluid source and adapted to allow fluid into the line from the fluid source. A pump is flow coupled to the intake downstream of the first valve and the second valve, and is operable to draw the sample from the source at a first flow rate and draw the sample from the line once injected with fluid at a second flow rate.

Other objects, features, aspects, and advantages of the invention will become apparent to those skilled in the art from the following detailed description and accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE FIGURES

Preferred exemplary embodiments of the invention are illustrated in the accompanying drawings in which like reference numerals represent like parts throughout.

In the drawings.

DETAILED DESCRIPTION OF THE INVENTION

Figure 1:
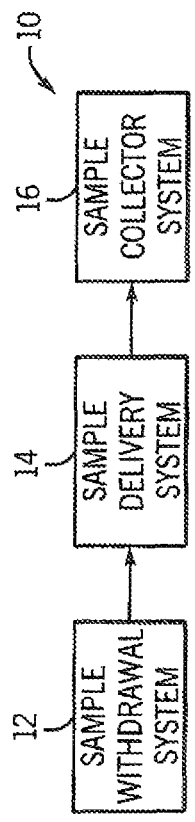
FIG. 1 is a block diagram of a segmented online sampling apparatus according to the present invention.

Referring briefly to FIG. 1, in one representative embodiment, a segmented online sampling apparatus 10 can be characterized as being comprised of three systems a sample withdrawal system 12, a sample delivery system 14, and a sample collector system 16. The sampling apparatus 10 may have multiple sample withdrawal systems 12 so that samples can be captured from multiple sources yet a single delivery system 14 may be used to deliver the captured sample to the collector system 16. Similarly, multiple delivery systems 14 may be used to deliver multiple samples to a single collector system 16. Each of these systems, and various alternate embodiments thereof, is described hereafter.

Multiline Sample Withdrawal System

Figure 2:
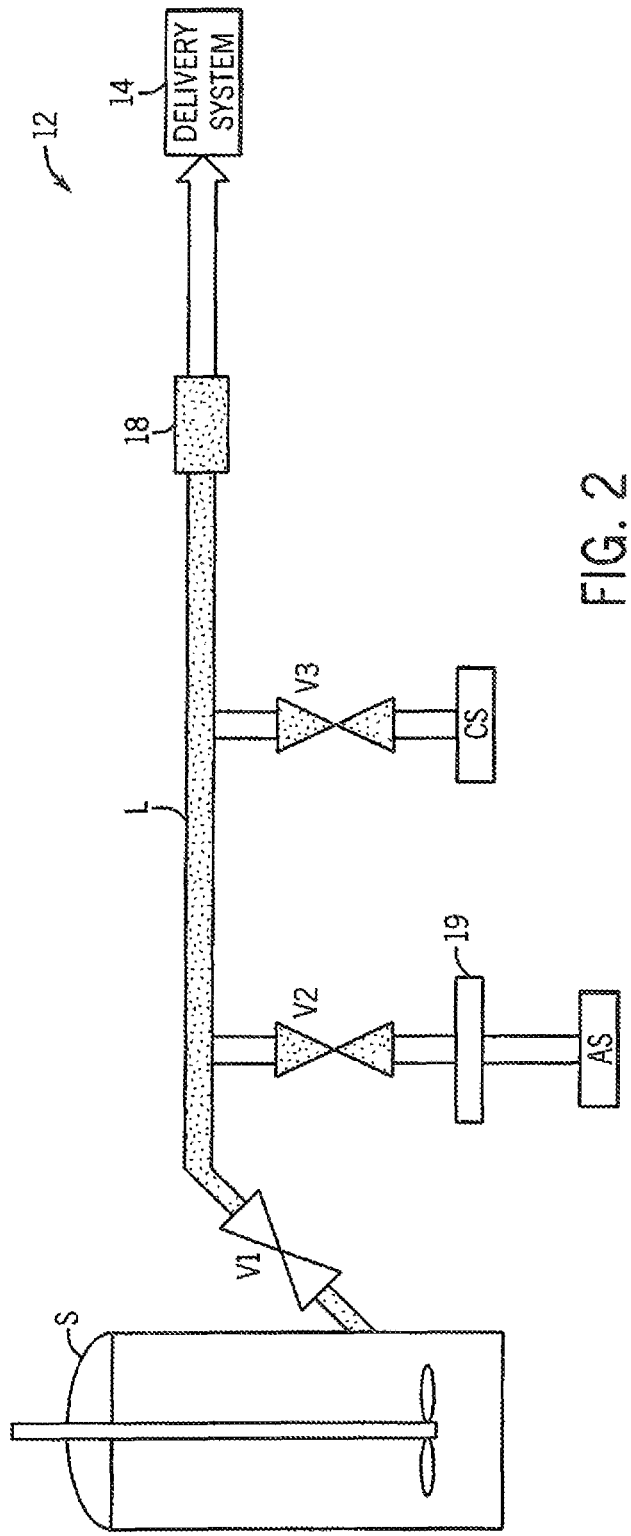
FIG. 2 is a schematic diagram of a sample withdrawal system of the segmented online sampling apparatus of FIG. 1.

Referring now to FIG. 2, the sample withdrawal system 12 interfaces with a source S to withdraw a sample using a suitable probe/port (not shown) and then deliver the sample in a controlled manner to the delivery system 14. For purposes of description, the term "source" shall include a chemical processing vessel, a bioreactor, fermentation vessel, process stream, water treatment vessel, or similar structure from which a sample may be taken. The sample withdrawal system 12 has three valves V1, V2, and V3 that are associated with the source 5, an air source AS, and a cleansing agent source CS, respectively. The sample withdrawal system 12 further has an inline sample indicator 18, such as a bubble detector, that indicates when a sample has been extracted from the source S. Air from the air source AS is preferably filtered by filter 19 before it is presented to line L. As will be described below, the valves V1, V2, and V3 are controlled to provide fluid management regarding the collection and the presentation of the sample to the delivery system 14.

Sample Delivery System

Figure 3:
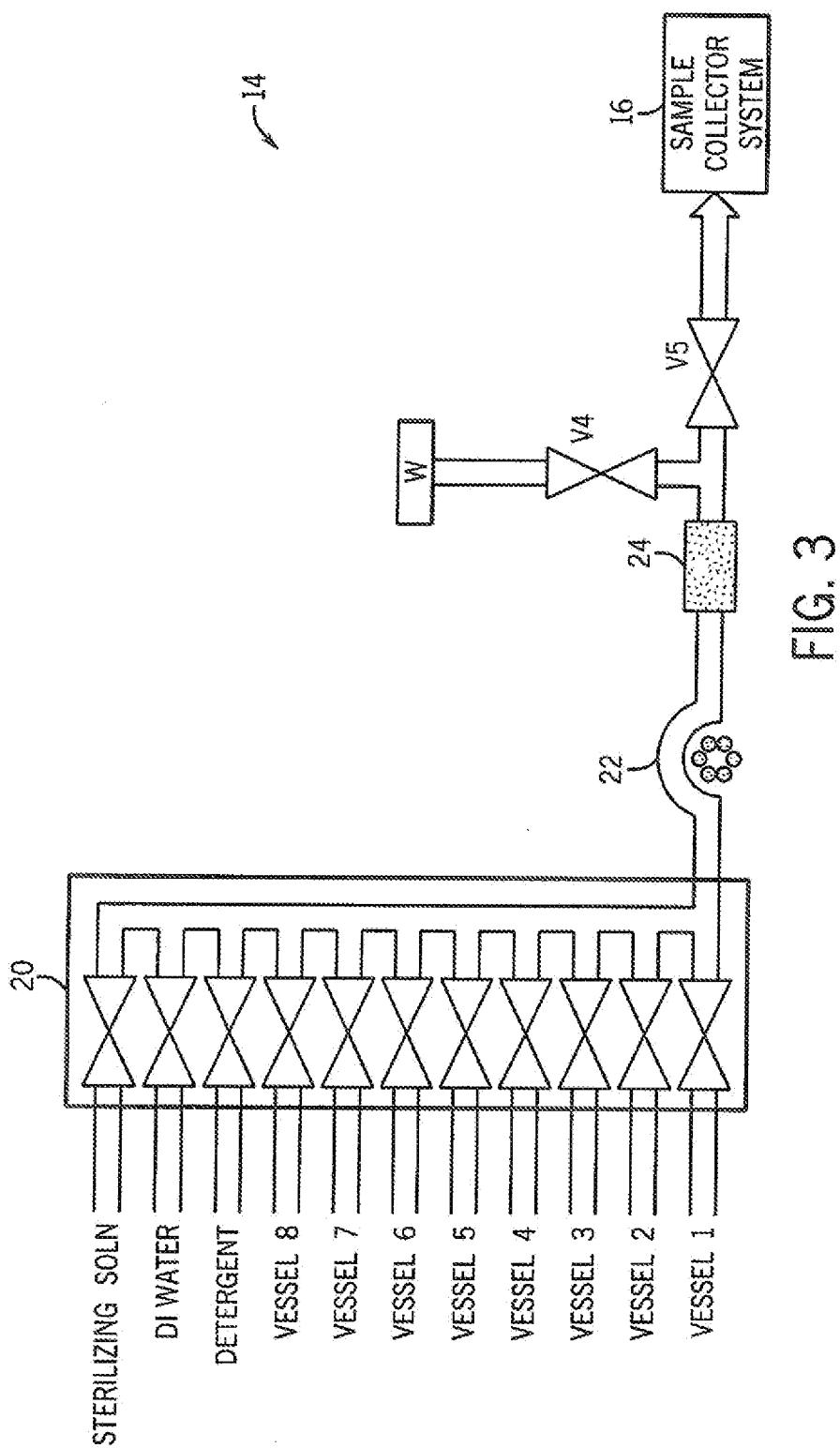
FIG. 3 is a schematic diagram of a sample delivery system of the segmented online sampling apparatus of FIG. 1.

Referring now to FIG. 3, the sample delivery system 14 generally includes a sample manifold 20 to which multiple sample withdrawal systems are connected so that a single flow system may be used to deliver a sample from multiple sources (Vessels 1, 2, 3, . . . n) to the same collector system 16. To reduce cross-contamination, the manifold 20 may be cleansed using detergent and then rinsed using sterilizing solution, as known in the art. A pump 22 communicates with the manifold 20 to draw a sample from the manifold 20. In a preferred embodiment, the pump 22 draws the sample from the manifold 20 at a rate that is faster than used to withdrawal the sample from the source. A bubble detector 24, or similar indicator, is located downstream of the pump and is used to indicate when the sample has been withdrawn from the manifold 20. Valves V4 and V5 control whether the sample is delivered to a waste receptacle W or the collector system 16, respectively.

Sample Collector System

Figure 4:
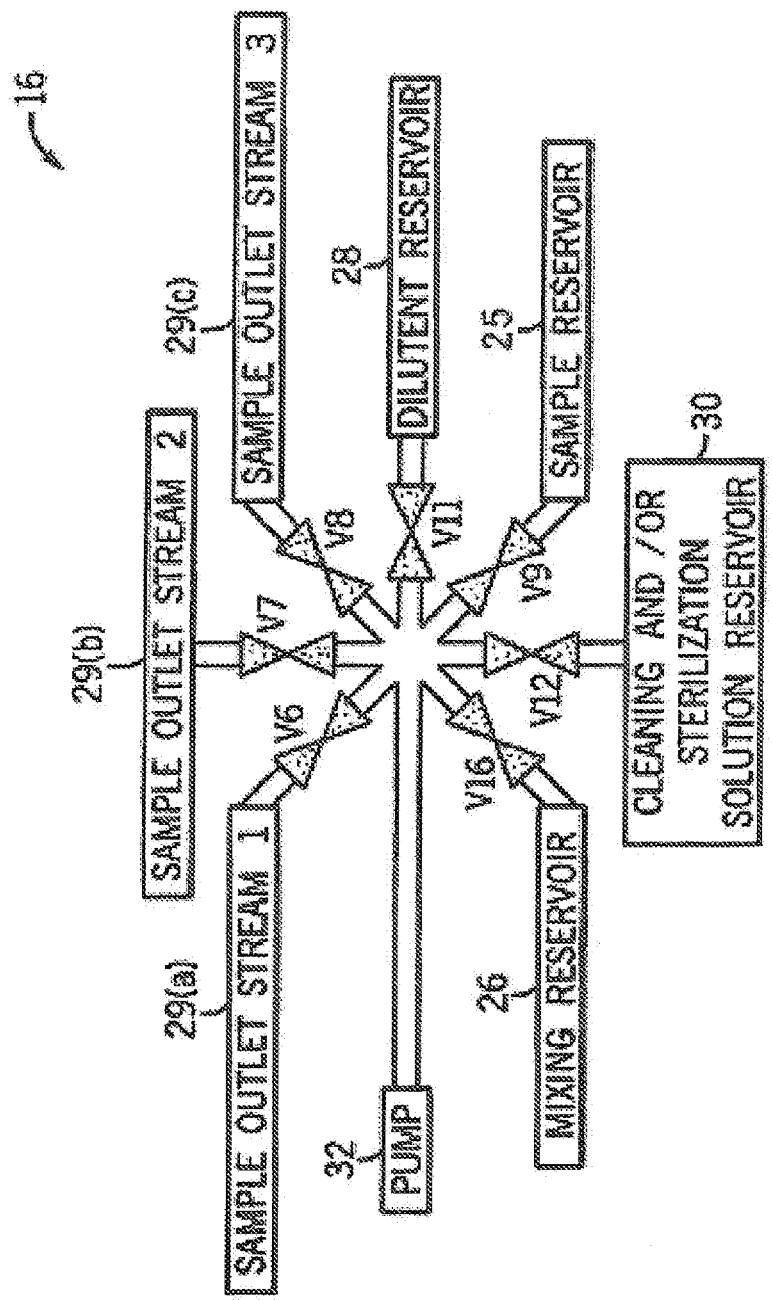
FIG. 4 is a schematic diagram of a collector system operative to receive samples from multiple delivery systems according to one aspect of the invention.

Referring now to FIG. 4, the collector system 16 is linked to receive samples from a delivery system. The sample from a delivery system 14 is deposited into a sample reservoir 24. The collector system 16 may also include a mixing reservoir 26, a dilutent reservoir 28, a cleansing and/or sterilization solution reservoir 30 and multiple sample outlet streams, 29(a), 29(b) and 29(c). A pump 32 is used to draw the test samples from the sample reservoir 24, dilutent from reservoir 28, and cleansing/sterilization solution from reservoir 30 and deliver samples to output streams 29(a), 29(b), or 29(c). Each outlet stream and each reservoir 24, 26, 28, and 30 includes a dedicated flow control valve (valves V6, V7, V8, V9, V10, V11, and V12, respectively). A sample indictor or bubble detector similar to sample indicators 18 and 24 may be used to determine if the dilutent and cleaning/sterilization solution reservoirs are full or needed refilling. It is preferred to read such a sample indicator prior to sampling to confirm their availability.

Stages of Operation

Stage 1: Pre-Sample Withdrawal

Referring briefly again to FIG. 2, in a first stage of operation, a waste sample is collected from the source S. The waste sample is captured by opening valve V1 with valves V2 and V3 closed. When the waste sample reaches the sample indicator 18, this signals that a sample is now in the line L and a controller (not shown) then determines how long the pump 22, FIG. 3, should run at a desired pump rate to draw a sample from the source S. The valve V1 then closes and valve V2 is opened to introduce filtered air into the line L. The pump 22 is then caused to pump at a much faster rate to increase the flow rate of the waste sample. When the injected air reaches the sample indicator 16, the pump 22 returns to its previous pump rate, and valve V2 is closed and valve V1 is opened. The delivery system 16 delivers the waste sample and air to a waste collector. The waste sample is used to assess the integrity of the system overall and, in particular, the pump, tubing and valves. More particularly, the time it takes for the waste sample to move from indicator 18 to indicator 24 is used to determine a flow rate and, if that flow rate is within set bounds, the system is suitable for sampling.

Stage 2: Sample Withdrawal

Figure 5:
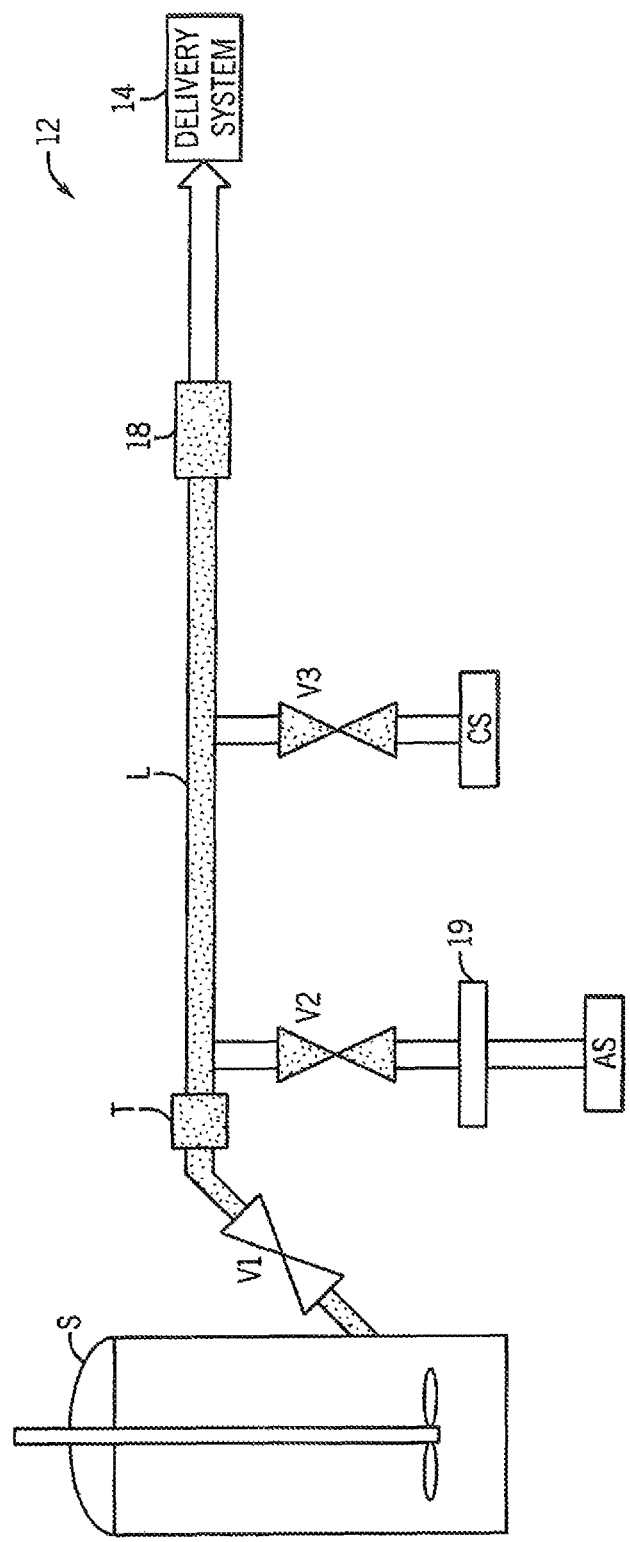
FIG. 5 is a schematic diagram of the sample withdrawal system of FIG. 2 shown during a sample withdrawal stage of a sampling process according to one aspect of the invention.
Figure 6:
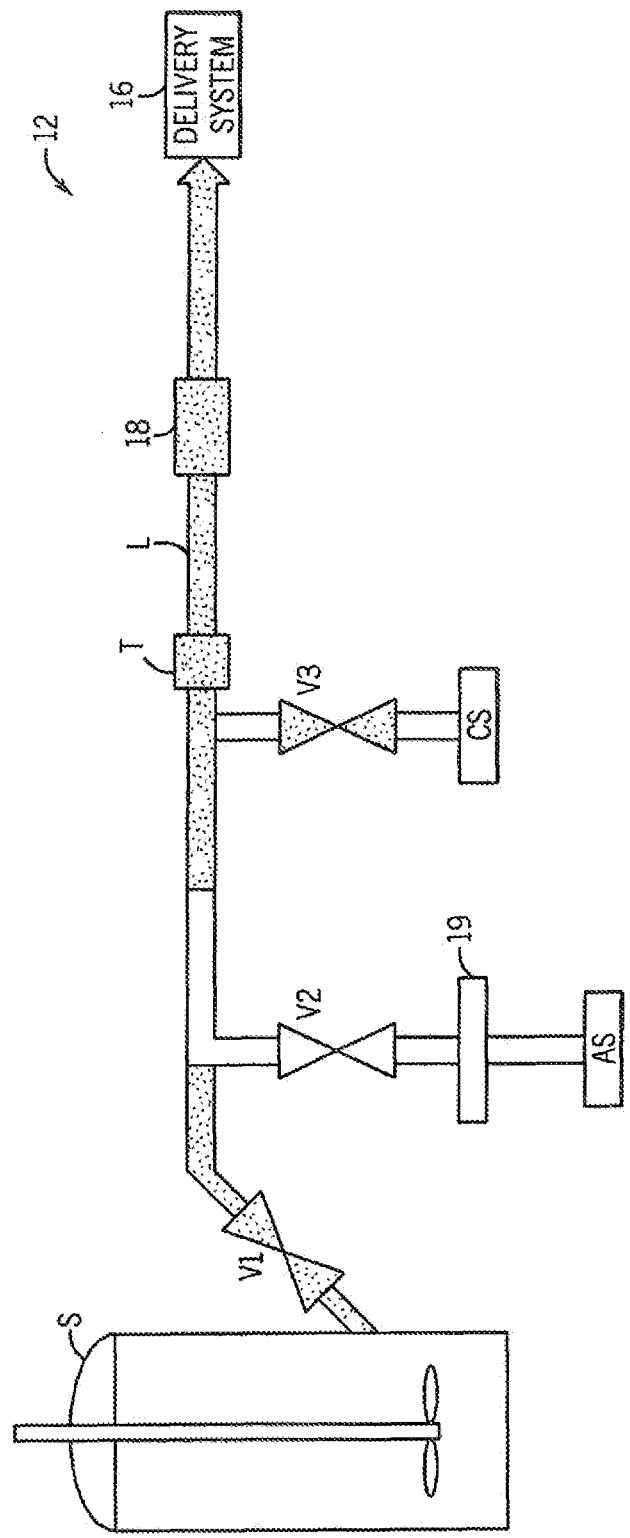
FIG. 6 is a schematic diagram of the sample withdrawal system of FIG. 2 shown during an air introduction stage of a sampling process according to one aspect of the invention.

Referring now to FIG. 5, with valve V1 open and valves V2 and V3 closed, a test sample T is withdrawn by activating the pump 22 of the sample delivery system 14 to a pump rate corresponding to the desired sample withdrawal rate, which is variable and is generally defined by the type of sample, the device the sample is drawn through (probe/port) and the composition of the sample to be withdrawn. Material is drawn from the source S until detected by the sample indicator 18. With reference now to FIG. 6, the valve V1 is then closed and valve V2 is opened to inject filtered air into line L. The pump 22 is then caused to pump at a faster, e.g., maximum, rate to increase the flow rate through the line L to expedite the delivery of the test sample T from the withdrawal system 12 to the collector system 16. The introduction of filtered air into the line L allows for a smaller test sample which can be delivered relatively expeditiously and, advantageously, allows the test sample to traverse over relatively lengthy distances without significantly affecting the chemical or biological properties of the test sample. In addition, samples can be taken from multiple sources without a long lag time between samplings.

Stage 3: Sample Delivery

Figure 7:
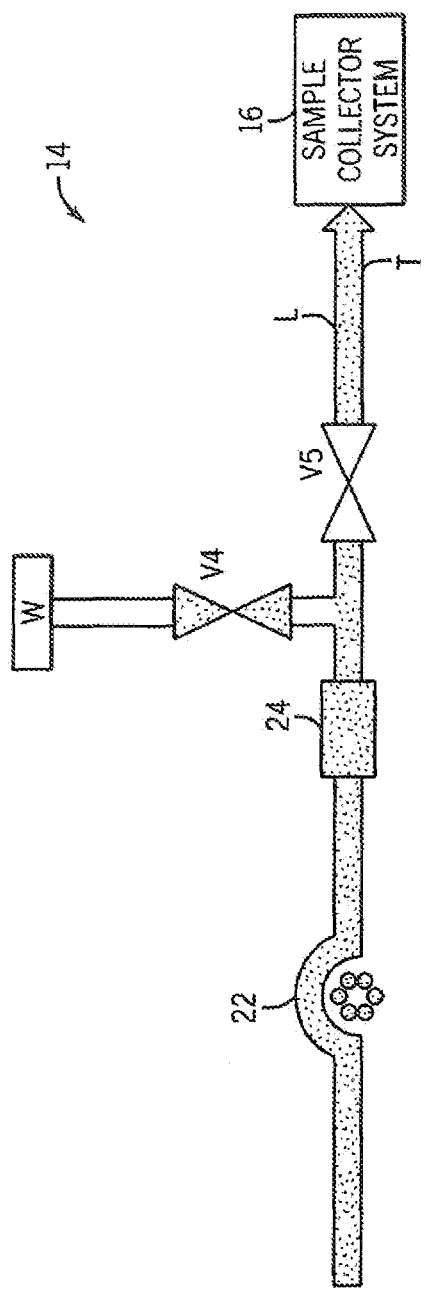
FIG. 7 is a schematic diagram of the sample delivery system of FIG. 3 shown during delivery of a sample to the sample collector system according to one aspect of the invention.

The test sample T is delivered to the corresponding input line of the manifold 20, FIG. 3. The pump 22 draws the test sample from the manifold 20, with valve V4 opened and valve V5 closed. However, when the sample reaches the sample indicator 24, valve V4 is closed and valve V5 opened as shown in FIG. 7. (It is noted that when the waste sample is purged from the line, valve V4 is left open and valve V5 is left closed so that the waste sample is delivered to the waste receptacle W.) With valve V4 closed and valve V5 open, the test sample is delivered to the collector system 16 for collection, storage, analysis, etc. It is contemplated that some type of sample preparation, such as dilution, may be carried out before the test sample T is delivered to the collector system 16.

Stage 4: Sample Collection

Referring back to FIG. 4, the test sample T is delivered to the collector system 16 whereupon the sample T is deposited into the sample reservoir 24 or sent directly to a collector or analyzer if no sample preparation is necessary or if only using one output stream 29 (collector/analyzer). The pump 32 can then draw material from the sample reservoir 24 as well as dilutent from reservoir 28 and deliver each to the mixing reservoir 26. The sample and the dilution solution are then mixed. Pump 32 draws the mixed solution from the mixing reservoir 26 and delivers it to the output streams 29(a), 29(b), and 29(c), wherein it is delivered to an analyzer, autosampler, or other type of post-capture collector of the sample collector system 16.

Stage 5: Post-Sample Collection

Figure 8:
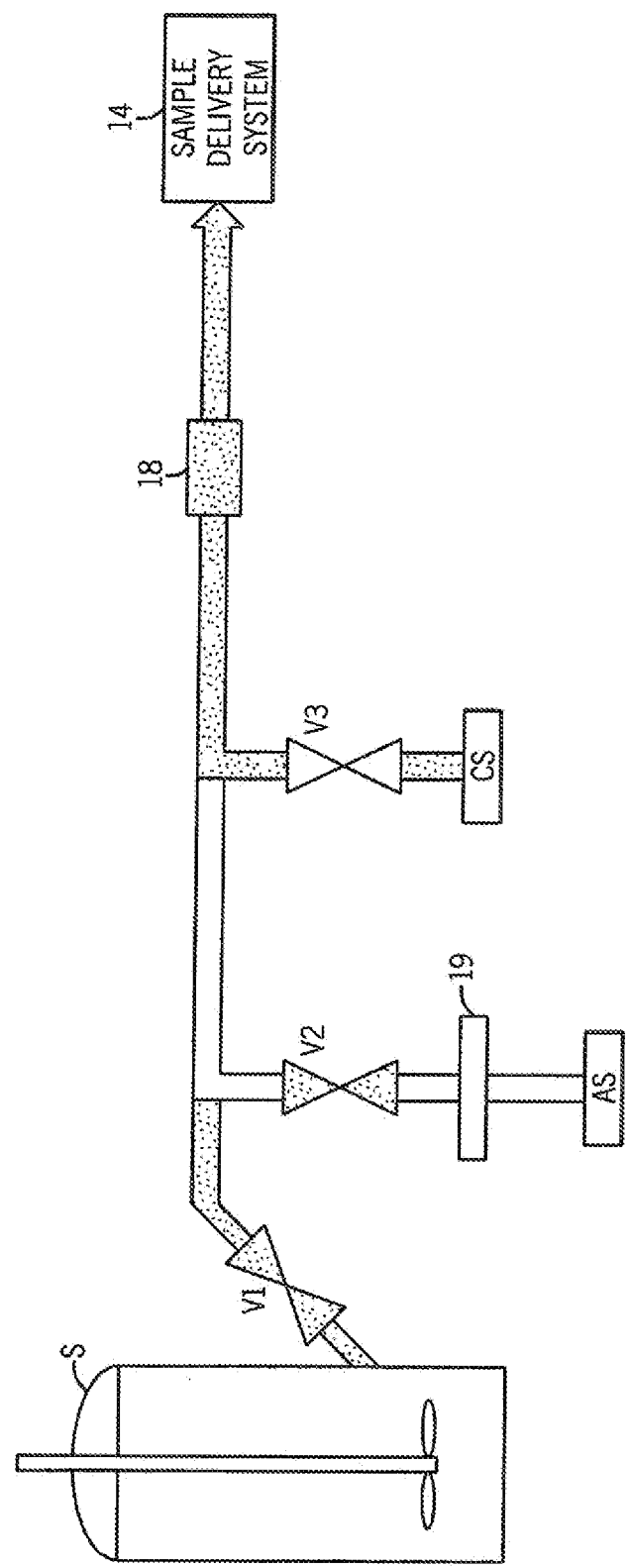
FIG. 8 is a schematic diagram of the sample withdrawal system of FIG. 2 shown during the introduction of cleansing and/or sterilization fluid according to another aspect of the invention.

Once the mixed sample is delivered to the output streams 29(a), 29(b), and 29(c), the line between the sample reservoir 24, the mixing reservoir 26, the lines therebetween, and the line that connects each to the delivery system 14 are preferably cleaned, rinsed and sterilized. In addition, the sample withdrawal system 12 and the sample delivery system 14 may be cleansed and sterilized by closing the air valve V2 and opening valve V3 to pump cleansing and sterilization solution from reservoir CS as shown in FIG. 8. Alternatively, it is contemplated that additional tubing, valves, reservoirs, and/or pumps can be added to the systems to deliver additional or alternative cleaning products to the sample withdrawal, sample delivery and sample collection systems. In an alternate embodiment, the tubing and valves could be discarded and replaced with new tubing and valves.

Figure 9:
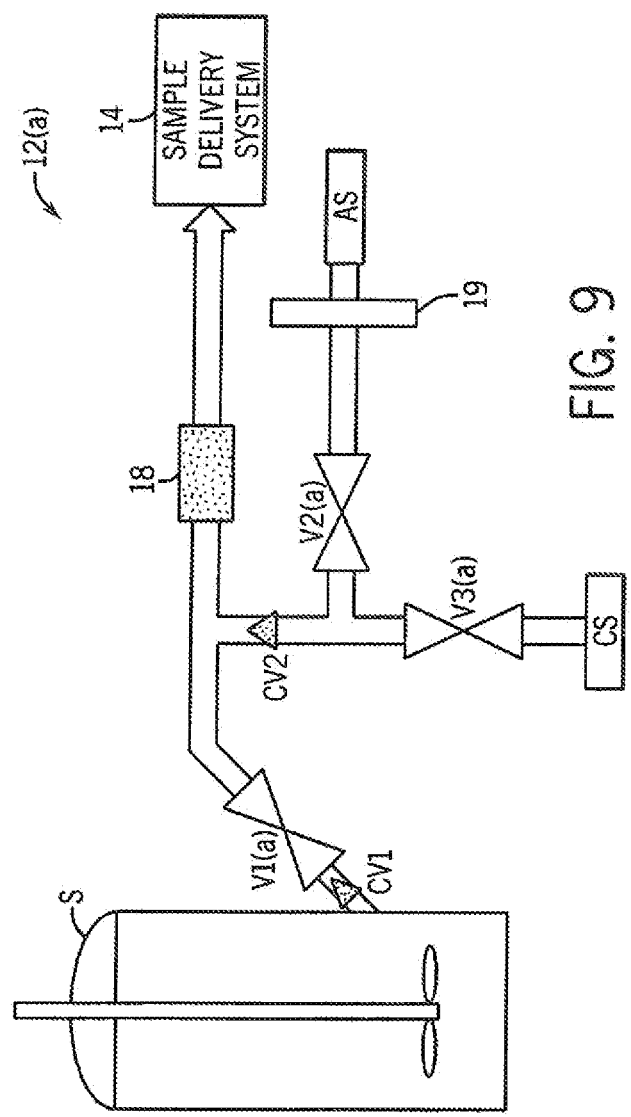
FIG. 9 is a schematic diagram of a sample withdrawal system according to an alternate aspect of the invention.
Figure 10:
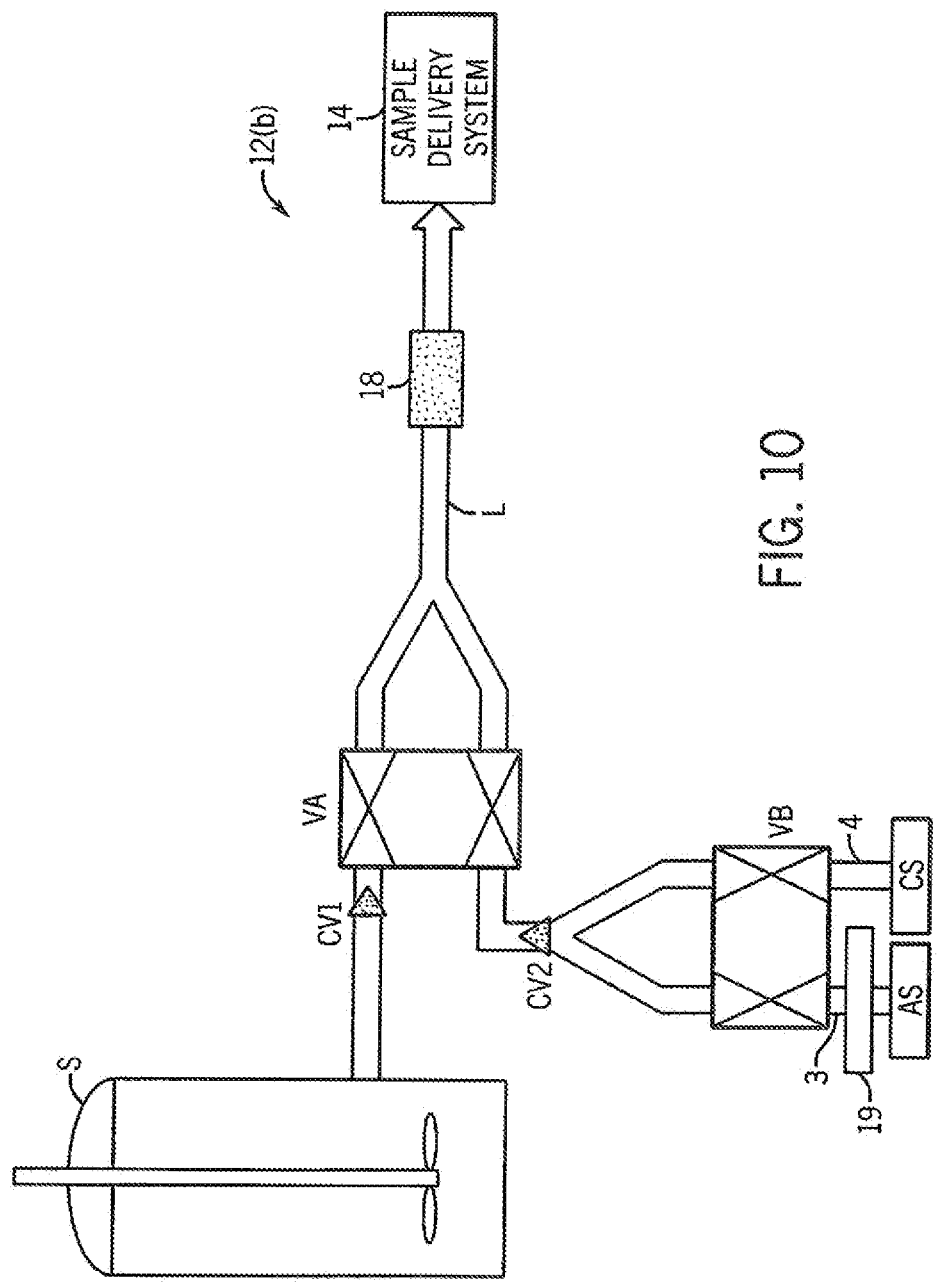
FIG. 10 is a schematic diagram of a sample withdrawal system according to yet another alternate aspect of the invention.

In the above-described apparatus, the sample and, more particular, cellular material of the sample, may come into contact with the sterilizing and/or cleaning solution. In another embodiment, illustrated in FIG. 9, the sample withdrawal system 12(a) has a differently arranged valve network comprised of valves V1(a), V2(a), and V3(a) and a check valve CV1 incorporated downstream of valve V1 and a check valve CV2 upstream of valves V2(a) and V3(a). In operation, valve V2(a) is opened and the pump 22 is turned on to remove any cleaning or sterilization solution from the line before a test sample is drawn from the source S. In yet a further embodiment, which is shown in FIG. 10, the sample withdrawal system 12(b) includes a pair of dual headed valves VA, VB. The air source AS and the cleansing agent source CS are flow-coupled to inputs 3 and 4 of the dual headed valve VB, respectively. The dual headed valve VA similarly has a pair of inputs 1 and 2, which are flow-coupled to the source S and the dual headed valve VB, respectively. Check valves CV1 and CV2 control the direction of flow of fluid to the inputs 1 and 2 of dual headed valve VA. One skilled in the art will appreciate that through selective closing and opening of the inputs to the dual headed valves VA and VB, a sample can be extracted, air injected into the system, and the system cleansed and/or sterilized.

Single Line Sampling Apparatus

Figure 11:
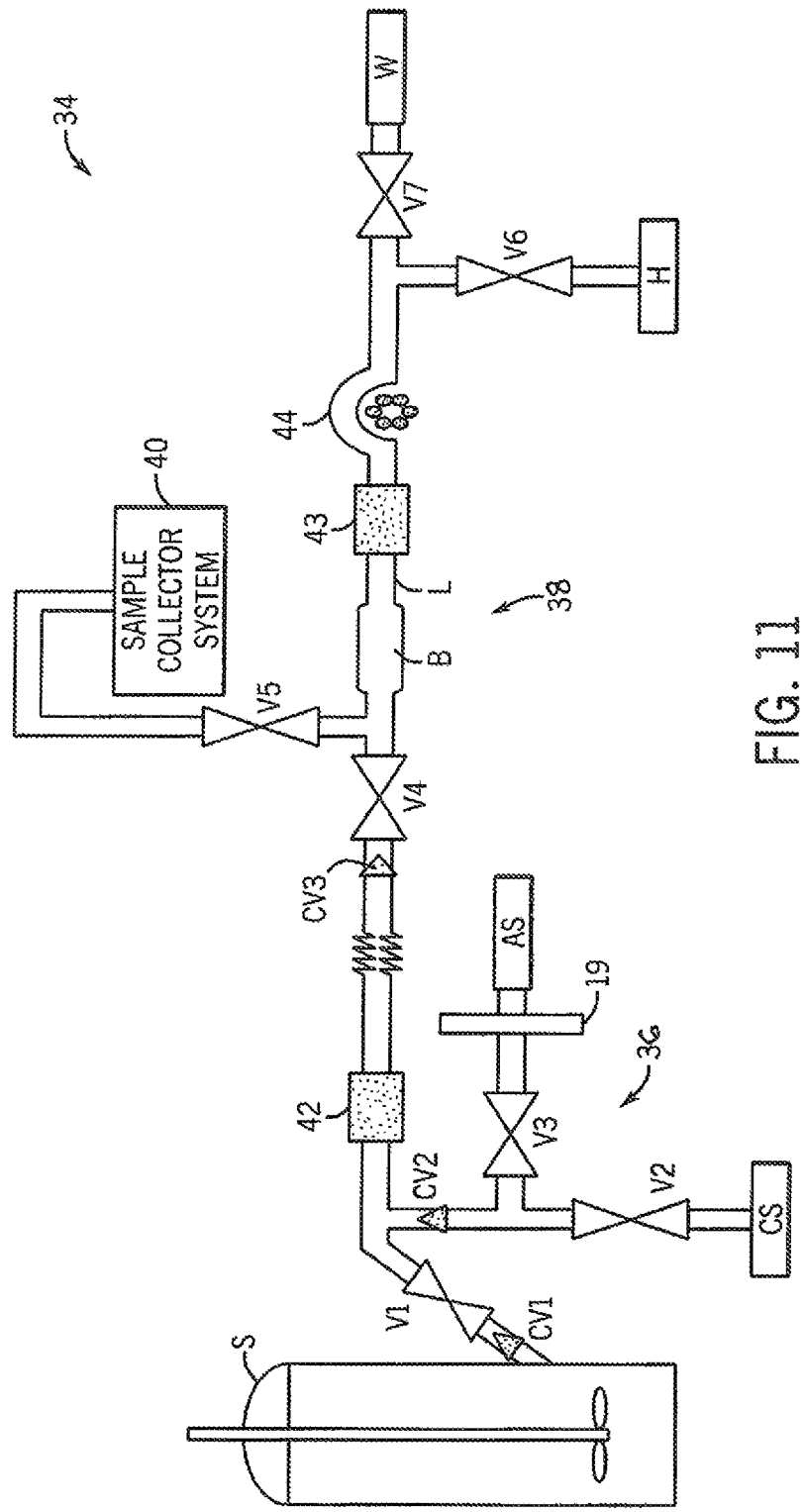
FIG. 11 is a schematic diagram of a segmented online sampling apparatus according to an alternate aspect of the invention.

The invention could also be embodied in a single line sampling apparatus 34 that is particularly applicable for those situations in which it is desired that the samples from one source S not come into contact with the samples of other sources. Similar to the multiline sampling apparatus 10, as shown in FIG. 11, the single line sampling apparatus 34 has a sample withdrawal system 36, a sample delivery system 38, and a sample collector system 40.

Sample Withdrawal System

The sample withdrawal system 36 includes a check valve CV1 that is connected inline between the source S and a valve V1. The sample withdrawal system 36 further has a valve V2 interconnected between the line L and a cleansing solution source CS, and a valve V3 interconnected between the line L and a filtered air source, AS. A check valve CV2 is connected inline upstream of valves V2 and V3. A sample indicator 42 is inline with the valves and is used to detect when a sample has been drawn from the source. In one embodiment, the sample indicator 42 is a bubble detector.

Sample Delivery System

Still referring to FIG. 11, the sample delivery system 38 includes check valve CV3 and a pair of flow control valves, valve V4 and V5, which control the flow of a sample from the sample withdrawal system 36 to the sample collector system 40. The sample delivery system 38 includes an adjustable volume bladder B (which could also be a tubing coil) that feeds into a sample indicator 43, such as a bubble detector. A bi-directional pump 44 draws fluid from the line L and delivers the fluid to either a waste receptacle W or a harvest receptacle H, as will be explained in greater detail below. Valves V6 and V7 control the flow of fluid to the harvest receptacle H and waste receptacle W, respectively. Sterile bags could be placed downstream of valve V6 for harvesting or sample collection. Thus, when valve V7 is closed, the sample is delivered to a sterile bag that can be handled in a suitable way for subsequent analysis. A dual headed valve (not shown) could also be used as a replacement for valves V6 and V7, such as that described above with respect to FIG. 10.

Sample Collector System

Figure 12:
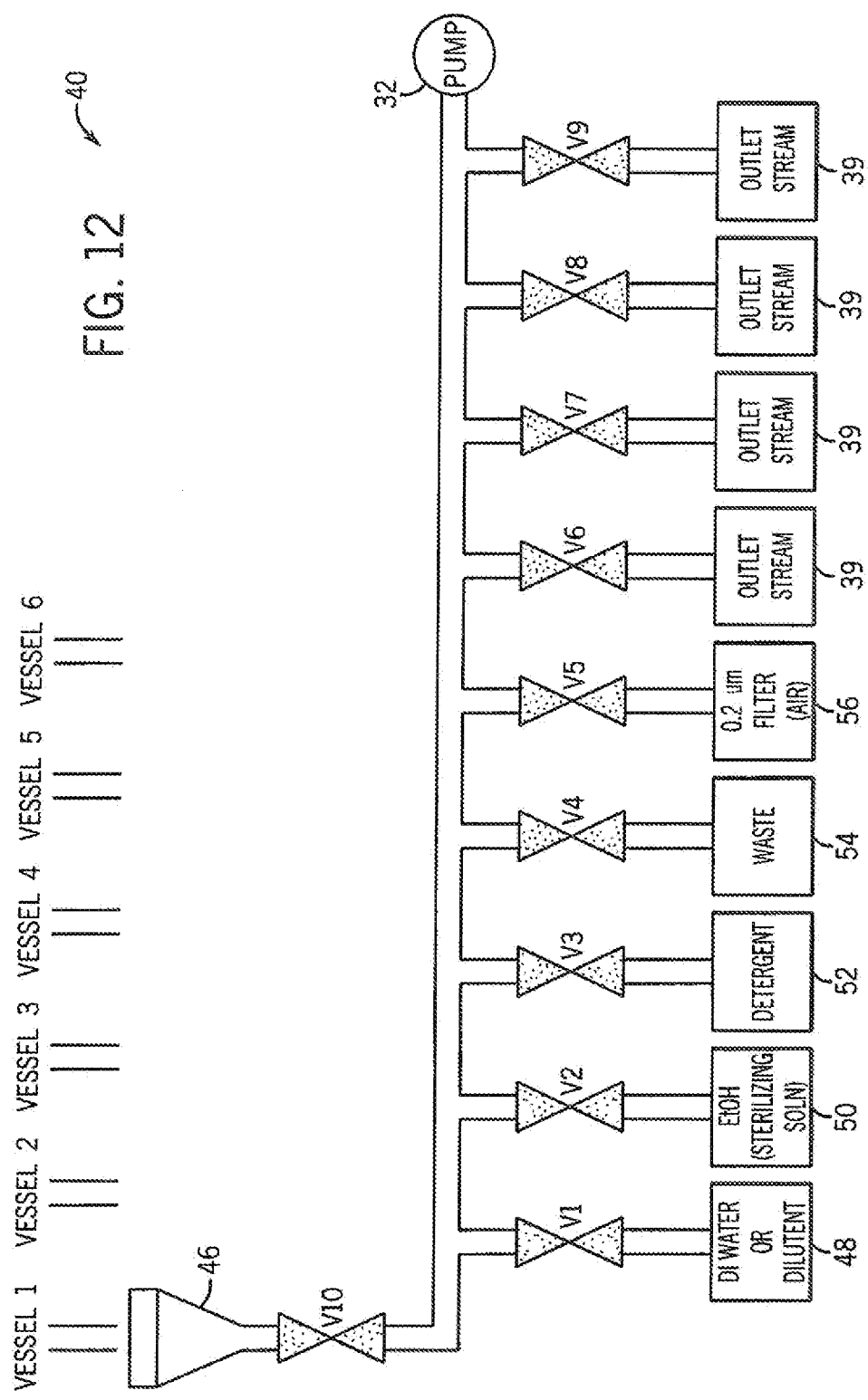
FIG. 12 is a schematic diagram of an autosampler/sample collection system for use with the sampling apparatus shown in FIG. 11.

The sample collector system 40, as shown in FIG. 12, includes a dispensing cup 46 into which the sample is deposited. A single dispensing cup 46 can be used to collect samples from multiple sources or vessels. However, to avoid cross-contact, the dispensing cup 46 does not come into contact with the delivery system 38 for each source. The dispensing cup 46 is similar in operation to the sample reservoir described with respect to the first embodiment of the invention.

The dispensing cup 46 is fluidly connected to a number of reservoirs and output streams 39. More particularly, a distilled water reservoir 48, a sterilizing solution reservoir 50, a detergent reservoir 52, a waste reservoir 54, an air source 56, and multiple delivery systems are capable of either supplying fluid to the dispensing cup 46 or receiving fluid from the dispensing cup 46. For instance, opening valves V1 and closing valves V2 through V10, dilutent can be drawn into the pump 32, then opening valve V10 and closing valves V1 through V9 allows the fluid from the reservoir 48 to be pumped into the dispensing cup 46. Similarly, sterilizing solution, detergent, and air may be pumped to the dispensing cup 46 by opening valves V2, V3, and V5, respectively. Drawing fluid from any of the lines into the pump, closing the corresponding valve, opening valve V4 and closing all other valves, the fluid may be pumped to the waste reservoir 54.

The dispensing cup 46 is also used as a mixing reservoir, similar to that described with respect to the first embodiment. In this regard, a sample can be mixed with a dilutent and then presented to one of the output streams by opening valve V10, drawing in the mixed sample, closing valve V10 and opening one of valves V6 through V9. To allow for an increase in the flow rate, remove fluid from lines, or deliver a precious amount of sample to the outlet streams, air may be injected by opening valve V5.

The dispensing cup 46 can be presented to the sample delivery system 14 of each source in one of a number of known ways, including, for example, a pulley system, a conveyor system, or a mechanized drive system.

Stages of Operation

Stage 1: Pre-Sample Withdrawal

Referring again to FIG. 11, the first stage in the single line apparatus preferably begins with the pumping of sterilizing solution throughout the systems. Valve V2 is opened and the pump draws EtOH and/or detergent from cleansing solution reservoir CS and delivers the cleansing fluid(s) throughout. Valve V2 is closed and valve V3 is opened to remove the cleansing fluid(s) so that the sample does not come into contact with the cleansing fluid(s).

Referring to FIG. 12, the dispensing cup 46 is also cleansed by opening valve V3, closing valves V1-V2 and V4-V10, detergent 52 is drawn into the pump 32, then opening valve V10 and closing valves V1 through V9 allows the detergent 52 to be pumped into the dispensing cup 46. Similarly this can be done with the DI Water 48 and sterilization solution 50 to clean the dispensing cup.

Stage 2: Waste Sample Withdrawal

Referring back to FIG. 11, a waste sample is collected from the source S. The waste sample is captured using a probe/port, as known in the art, with valve V1 open and with valves V2 and V3 closed. When the waste sample reaches the sample indicator 42, this signals that a sample is now in the line L and the controller (not shown) then determines how long the pump 44 should run at a desired pump rate to draw the desired amount of sample from the source S. The valve V1 then closes and valve V3 is opened to introduce filtered air into the line L. The pump 44 is then caused to pump at a much faster rate to increase the flow rate of the waste sample. When the injected air reaches the sample indicator 42, the pump 44 returns to its previous pump rate, and valve V3 is closed and valve V1 is opened. The waste sample is used to assess the integrity of the system overall and, in particular, the pump, tubing and valves. More particularly, the time it takes for the waste sample to move from indicator 42 to indicator 43 is used to determine a flow rate and if that flow rate is within set bounds, the system is suitable for sampling.

Stage 3: Test Sample Withdrawal

With valve V1 open and valves V2 and V3 closed, a test sample is withdrawn using a suitable probe/port and by activating the pump 44 to a pump rate corresponding to the desired sample withdrawal rate, which is variable and is generally defined by the type of sample, the device the sample is drawn through (probe/port) and the composition of the sample to be withdrawn. Material is drawn from the source S until detected by the sample indicator 42. When the test sample reaches the sample indicator 42, this signals that a sample is now in the line L and the controller (not shown) then determines how long the pump 44 should run at a desired pump rate to draw the desired amount of sample from the source S. The valve V1 is then closed and valve V3 is opened to inject filtered air into line L. The introduction of filtered air allows the pump 44 to pump at a faster, e.g., maximum, rate to increase the flow rate through the line L to expedite the delivery of the test sample from the withdrawal system 36 to the sample delivery system 38. In this regard, with the introduction of filtered air to deliver the sample, the size of the sample withdrawn from the source S is smaller and allows the test sample to traverse lengthy distances without significantly affecting the chemical or biological properties of the test sample.

Stage 4: Test Sample Delivery

Before the test sample reaches the sample delivery system 38, the pump delivers all fluids drawn from the sample withdrawal system 36 toward the waste receptacle W downstream of valve V7. When the sample indicator 42 signals that a fresh test sample has been captured, the pump 44 is stopped and valve V4 is closed and valve V5 is opened. The pump 44 is then caused to pump fluid in a reverse direction to deliver any sample through valve V5 to the sample collector system 40. This is done to prevent the fresh sample from coming into contact with the rollers on the pump because, if the sample contains cells, they could be damaged by coming in contact with the rollers. Once the sample has been delivered to the sample collector system 40, the pump 44 is turned off, valve V5 is closed, valves V2 and V4 are opened, and then the pump 44 is turned on in the reverse direction moving cleaning/sterilization fluid(s) through the line and out to the waste receptacle W. When the sample indicator 43 signals the arrival of the cleaning/sterilization fluid(s), the pump 44 is stopped and valves V2 and V4 are closed, and valve V5 is opened. The pump 44 is then turned on in the reverse direction so that the cleansing/sterilization fluids are delivered through valve V5 until the tubing above valve V5 is filled. The cleansing/sterilization fluid(s) will remain in the tubing upstream of valve V5 until the next fresh sample is delivered to the sample collector system 40. This will reduce the possibility of contamination. After the process in source S is completed, the material in source S can be delivered to the harvest reservoir and pumped, with valves V1, V4 and V6 open and valves V5 and V7 closed, to the collector system. Alternately, the contents of the harvest reservoir or port H could be directly delivered to the sample collector system 40 or other collector system. If the sample is sensitive to the rollers on the pump 44, the harvest port H could be placed upstream of the pump.

Stage 5: Sample Collection

The fresh sample is pumped to the sample collector system 40, also referred to as an autosampler. The sample may be prepared using dilutent. The sample can then be delivered to one or more output streams that deliver the prepared sample to an analyzer for analysis or a collector for storage.

Stage 6: Post-Sample Collection

The tubing and the associated components are then cleansed, as described previously, using suitable cleansing agents and detergents. Alternately, the tubing could be single use, disposable tubing and thus may be replaced rather than cleansed following sample collection.

Alternative Embodiments

Figure 13:
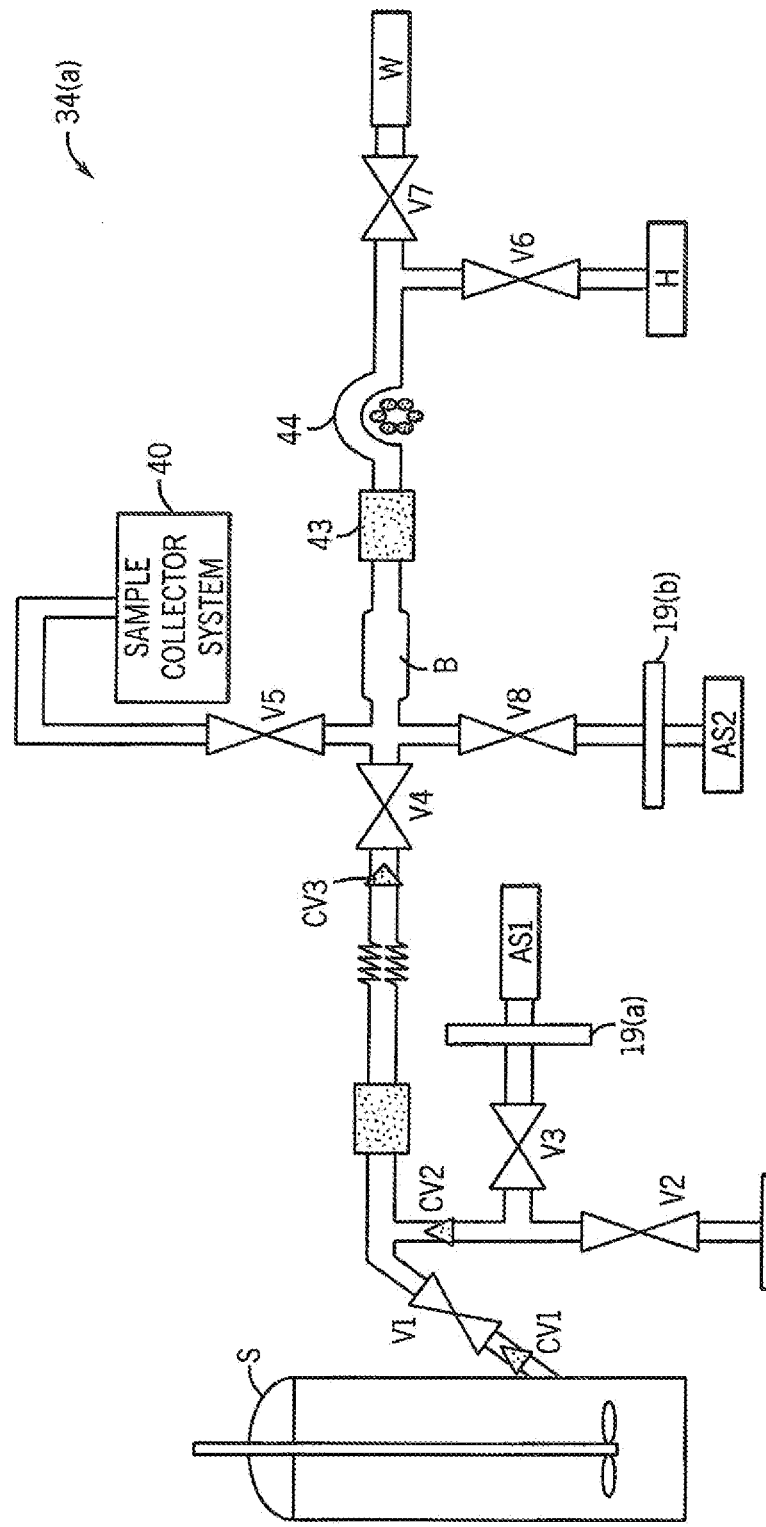
FIG. 13 is a schematic diagram of a segmented online sampling apparatus according to yet another alternate aspect of the invention.

FIG. 13 illustrates one alternate embodiment of a sampling apparatus 34(a) in which two air sources AS1 and AS2 are used to inject air into the system. Filters 19(a) and 19(b) function to filter air provided by the air sources AS1 AS2, respectively. Valve V8 controls the injection of air from air source AS2 into the system. Injecting air into the line by opening valve V8 allows a sample being held in either the harvest or waste receptacles to be pumped to the collector system 16 at a faster rate. When valve V4 is closed, air injected by air source AS1 is blocked from being used to deliver the sample to the collector system 16 from either of the harvest or waste receptacles. By having valves V7 and V8 open when the sample is not being withdrawn or delivered, multiple single line sampling apparatus may be used on one pump head.

Figure 14:
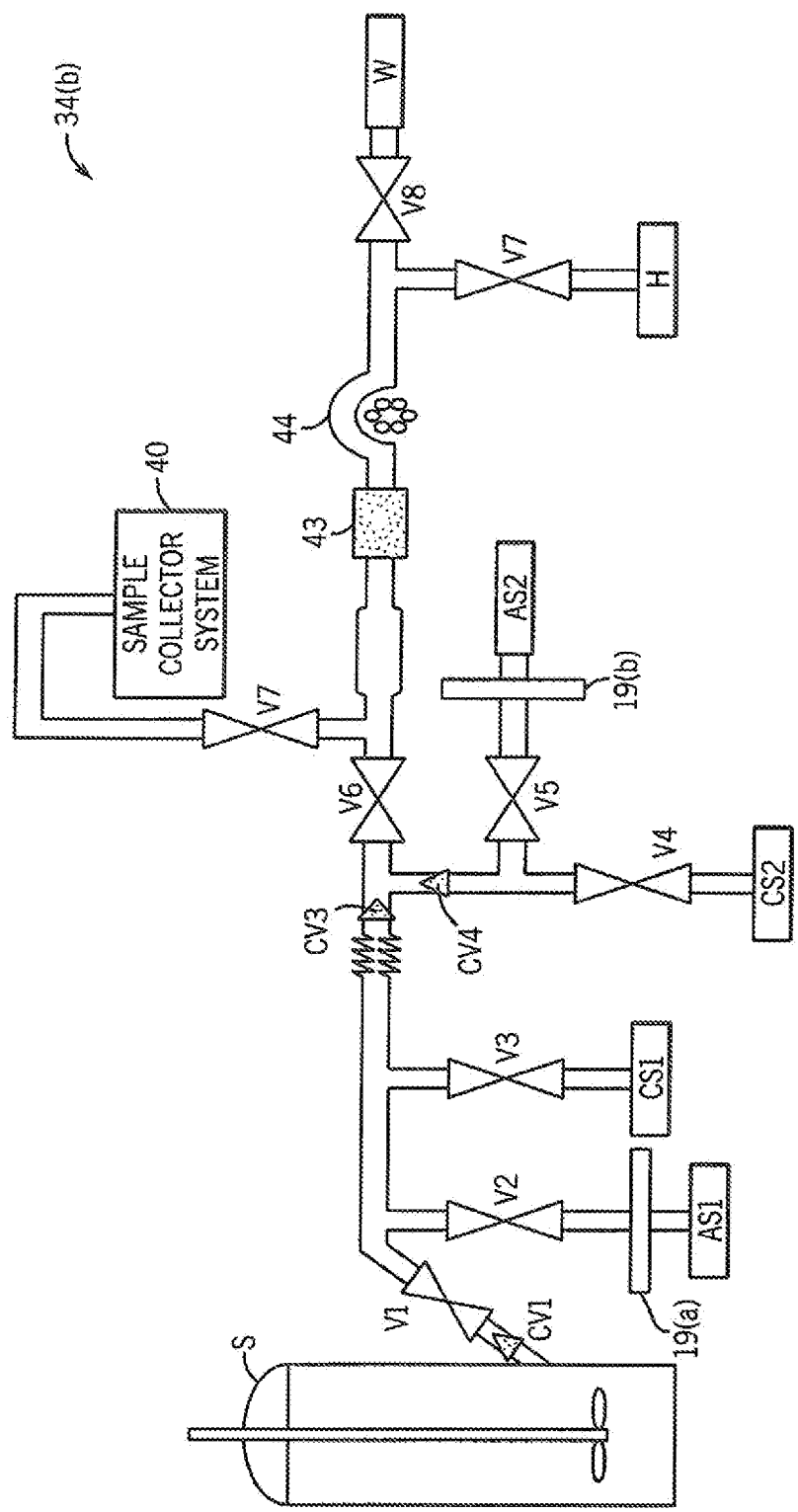
FIG. 14 is a schematic diagram of a segmented online sampling apparatus according to another aspect of the invention.

FIG. 14 illustrates yet another alternate embodiment of a sampling apparatus 34(b) having two air sources AS1 and AS2 and two cleansing/sterilizing agent sources CS1 and CS2. Having two air sources and two cleansing/sterilizing agent sources eliminates the need to move cleansing/sterilizing agent all the way from the sample withdrawal system.

In the embodiments described above, the sampling system 10 has a dedicated waste receptacle to which a waste sample and air injected to pass the waste sample may be delivered. It is contemplated however that the system may not have a dedicated waste receptacle and instead may use a waste receptacle that is part of the collector system 16, as described above. In this regard, as shown in FIG. 15, there is not a waste receptacle between the sample delivery system 14 and the sample collector system 16.

Figure 15:
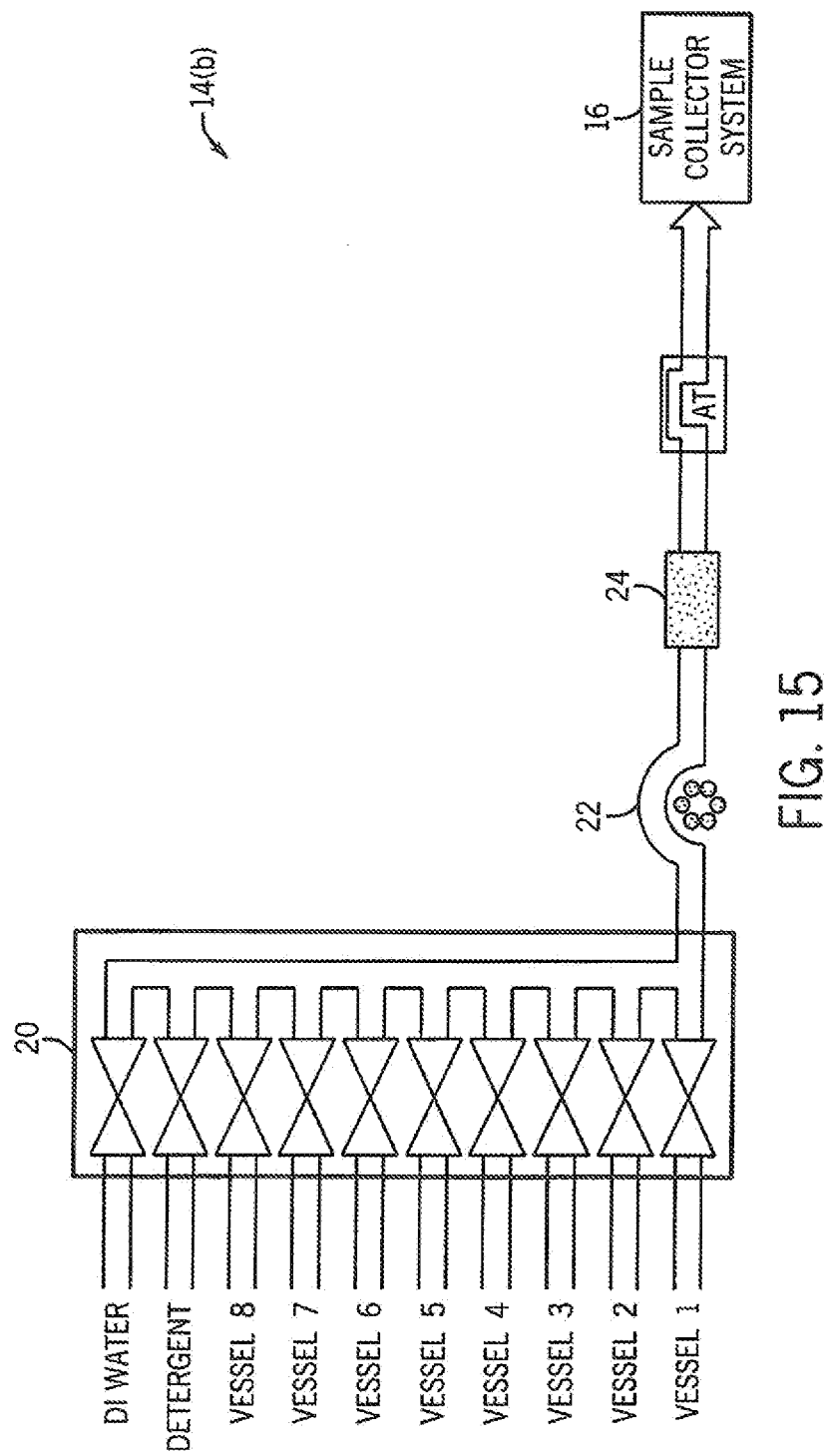
FIG. 15 is a schematic diagram of a sample delivery system according to another aspect of the invention.
Figure 16:
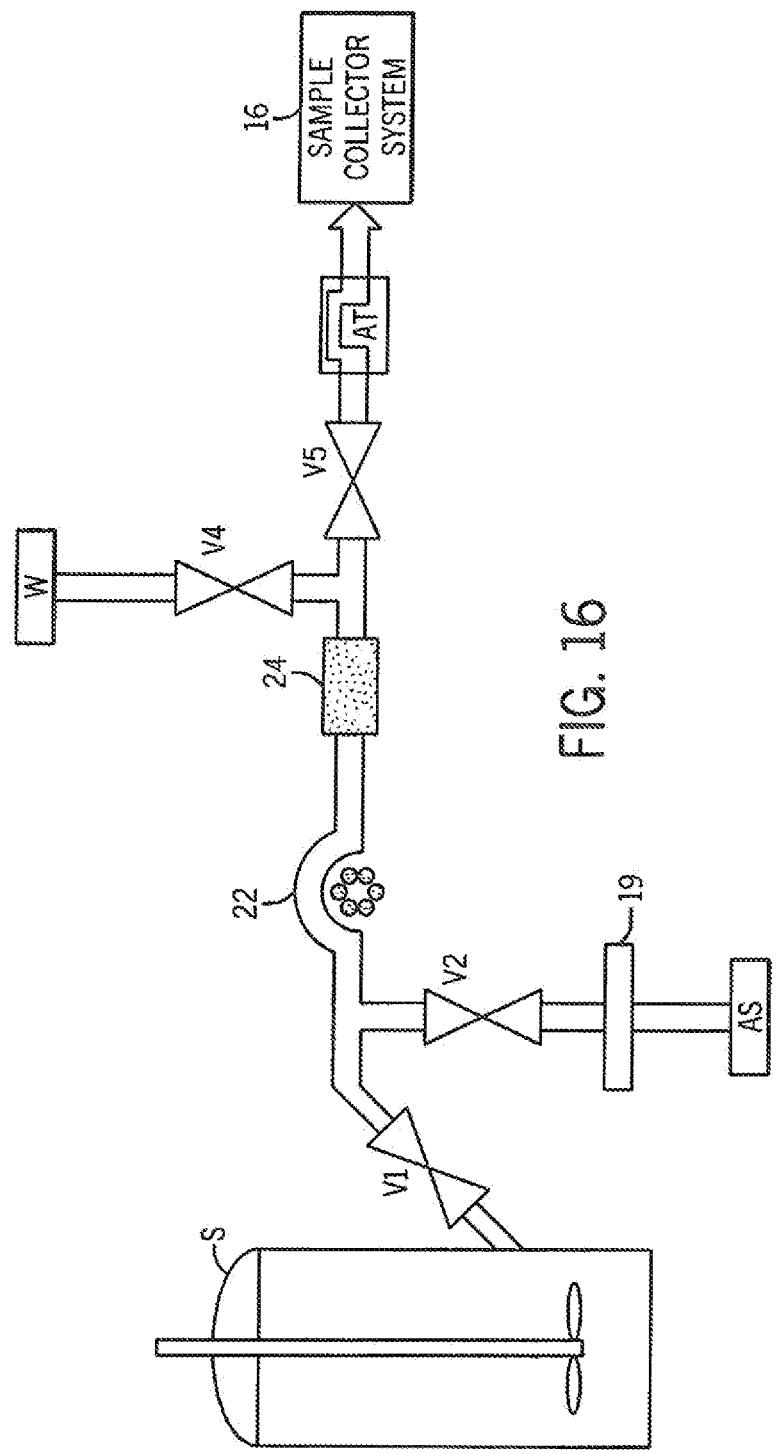
FIG. 16 is a schematic diagram of a sample delivery system according to another aspect of the invention.
Figure 17:
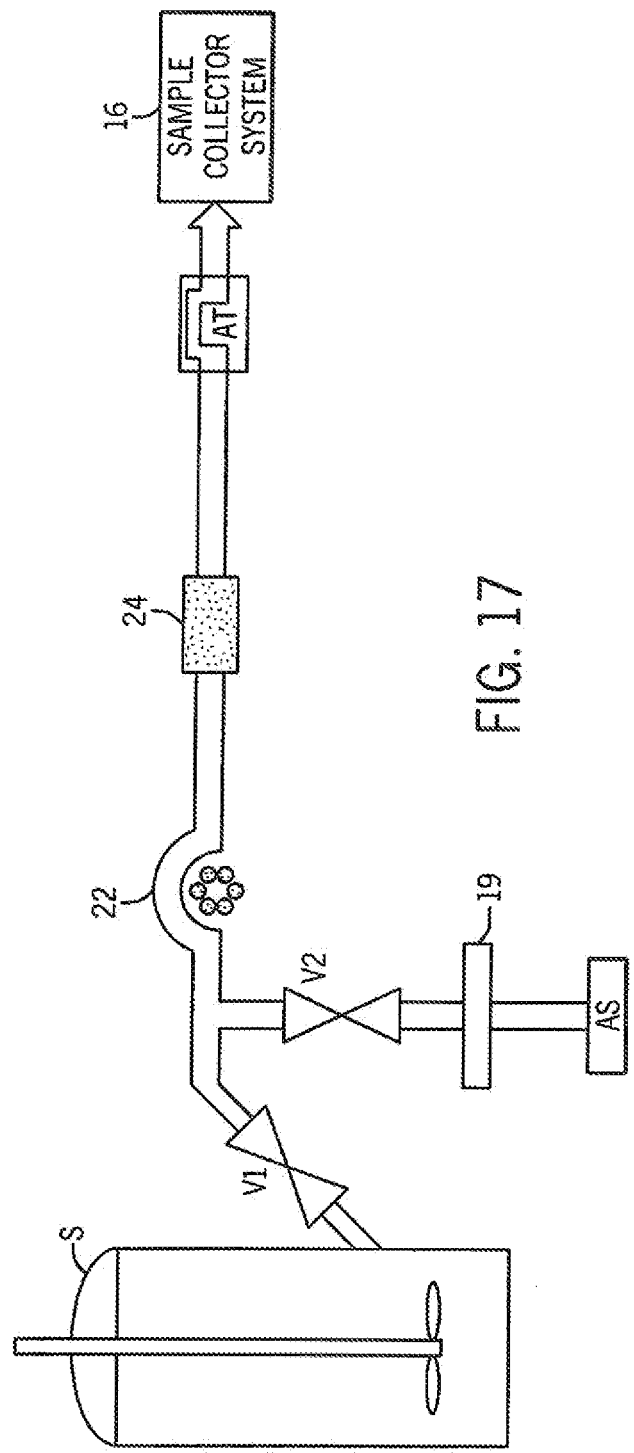
FIG. 17 is a schematic diagram of a sample delivery system according to another aspect of the invention.

Moreover, as also illustrated in FIGS. 15-17, an air trap AT may be used to remove air entrained in the sample as the sample passes through the air trap AT.

FIGS. 3 and 15-17 illustrated the sample indicator 24 as being downstream of the pump 22, but it is understood that the sample indicator 24 could be upstream of the pump 22.

Combined Sample Delivery and Sample Collector Systems

It will be appreciated that the various systems of the sampling apparatus 10 may be contained within a common or shared housing or in separate housings. For example, the delivery system 14 and the sample collector system 16 can be contained in a common housing. Alternately, the sample delivery system 14 and the sample collector system 16 may be integrated into a single layer of a shared housing.

It is noted that rather than using the head of the pump to draw in fluid, a coil could be used. Using a coil to draw in fluid rather than the pump ensures that the coil is flushed before new fluid is passed through the coil.

In one preferred implementation, the tubing and various valves described herein are color-coded to simplify assembly and installation, as well as to reduce improper connection of the tubes and the valves. Additionally, single use, disposable tubing could be used in order to alleviate the need to clean and sterilize the tubing and valves after each sampling and, thus, alleviate the need for a cleansing and/or sterilization source flow-coupled to the system, as illustrated in FIGS. 16 and 17.

Multi-channel/lumen tubing could be used for line L. This would allow delivery of two samples to the sample delivery system on one line from the sample withdraw system on one source S. For example, this could be a cell and cell-free sample from the same source S. Beside samples, cleaning/sterilization fluid from the sample delivery system/sample collector system could be sent to the sample withdrawal system. This would eliminate the need to have a cleaning/sterilization fluid reservoir at the sample withdrawal system. One reservoir at the sample delivery system/sample collector system could be used for multiple sample withdrawal systems.

A sample indicator, such as a bubble detector can be used one each of the diluent, sterilization solution, or detergent lines to verify that the fluid is currently available. The controller (not shown) would check the sample indicators before a sample is drawn out of source S to verify that the system is ready to operate properly.

Many changes and modifications could be made to the invention without departing from the spirit thereof. The scope of these changes will become apparent from the appended claims.

I claim:
1. A method of capturing a sample from a source and delivering the sample to a collector, comprising:
   drawing a sample from the source into a conduit;
   advancing the sample within the conduit in a downstream direction toward a sample indicator, wherein the sample defines a leading end that approaches the sample indicator as the sample is advanced in the downstream direction;
   indicating the presence of the sample within the conduit using the sample indicator when the sample attains a predetermined position within the conduit relative to the sample indicator;
   injecting a gas into the conduit in response to the indication of the presence of the sample within the conduit, wherein the injection of the gas into the conduit forms a sample bolus between the downstream end of the sample and an upstream end of the sample formed by the injection of the gas into the conduit;
   advancing the sample bolus together with the injected gas in the downstream direction past the sample indicator; and
   delivering the sample bolus and the injected gas to the collector.
2. The method of claim 1 wherein the sample bolus is drawn from the source at a first flow rate and the sample bolus and injected gas are advanced past the sample indicator at a second flow rate faster than the first flow rate.

3. The method of claim 1 further comprising passing cleansing and/or sterilization fluid through the conduit after the sample bolus has been delivered to the collector.

4. The method of claim 1 wherein the step of injecting a gas into the conduit comprises injecting air into the conduit.

* * * * *